(12) United States Patent
Gascoyne et al.

(10) Patent No.: US 7,033,473 B2
(45) Date of Patent: *Apr. 25, 2006

(54) METHOD AND APPARATUS FOR COMBINED MAGNETOPHORETIC AND DIELECTROPHORETIC MANIPULATION OF ANALYTE MIXTURES

(75) Inventors: Peter R. C. Gascoyne, Bellaire, TX (US); Jody V. Vykoukal, Houston, TX (US); Frederick F. Becker, Houston, TX (US)

(73) Assignee: Board of Regents, University of Texas, Austin, TX (US)

( * ) Notice: Subject to any disclaimer, the term of this patent is extended or adjusted under 35 U.S.C. 154(b) by 663 days.

This patent is subject to a terminal disclaimer.

(21) Appl. No.: 09/882,805

(22) Filed: Jun. 14, 2001

(65) Prior Publication Data

US 2002/0036141 A1    Mar. 28, 2002

Related U.S. Application Data

(60) Provisional application No. 60/211,757, filed on Jun. 14, 2000.

(51) Int. Cl.
*G01N 27/26* (2006.01)
*G01N 27/72* (2006.01)

(52) U.S. Cl. ..................... 204/547; 204/643
(58) Field of Classification Search ............... 204/547, 204/643
See application file for complete search history.

(56) References Cited

U.S. PATENT DOCUMENTS

| | | | |
|---|---|---|---|
| 4,001,102 A | 1/1977 | Batha et al. | 204/186 |
| 4,326,934 A | 4/1982 | Pohl | 204/180 |
| 4,440,638 A | 4/1984 | Judy et al. | 210/198.2 |
| 4,911,806 A * | 3/1990 | Hofmann | 204/545 |
| 5,344,535 A | 9/1994 | Betts et al. | 204/183.1 |
| 5,454,472 A | 10/1995 | Benecke et al. | 209/127.1 |
| 5,489,506 A | 2/1996 | Crane | 435/2 |
| 5,569,367 A | 10/1996 | Betts et al. | 204/547 |
| 5,571,401 A | 11/1996 | Lewis et al. | 205/787 |
| 5,653,859 A | 8/1997 | Parton et al. | 204/450 |

(Continued)

FOREIGN PATENT DOCUMENTS

EP    0513064    11/1992

(Continued)

OTHER PUBLICATIONS

Goater et al., "A combined travelling wave dielectgrophoresis and electrorotation device: applied to the concentration and viability determination of cryptosporidium," *J. Phys. D: Appl. Phys.*, 30:L65-L69, 1997.

(Continued)

*Primary Examiner*—Nam Nguyen
*Assistant Examiner*—Jeffrey Barton
(74) *Attorney, Agent, or Firm*—Fulbright & Jaworski LLP

(57) ABSTRACT

Methods and apparatuses for discriminating matter utilizing dielectrophoresis combined with magnetophoresis. A sample having one or more constituents is injected into an inlet port of a chamber. A carrier medium flow is initiated at the inlet port to establish a flow within the chamber. A dielectrophoretic force is generated to act on the constituents of the sample. A magnetophoretic force is generated to act on the constituents of the sample. The dielectrophoretic force and magnetophoretic forces are balanced to position the constituents within the chamber. The constituents are then collected at one or more outlet ports of the chamber according to the dielectric and magnetic characteristics of the constituents. The constituents may be collected as a function of time-of-exit from the chamber and/or position within the chamber.

18 Claims, 9 Drawing Sheets

U.S. PATENT DOCUMENTS

| | | | | |
|---|---|---|---|---|
| 5,683,569 | A | 11/1997 | Chung et al. | 205/775 |
| 5,814,200 | A | 9/1998 | Pethig et al. | 204/547 |
| 5,858,192 | A | 1/1999 | Becker et al. | 204/547 |
| 5,888,370 | A | 3/1999 | Becker et al. | 204/643 |
| 5,932,097 | A * | 8/1999 | Wilson | 210/222 |
| 5,965,452 | A | 10/1999 | Kovacs | 436/149 |
| 5,993,630 | A | 11/1999 | Becker et al. | 204/547 |
| 5,993,631 | A | 11/1999 | Parton et al. | 204/547 |
| 5,993,632 | A | 11/1999 | Becker et al. | 204/547 |
| 6,010,616 | A | 1/2000 | Lewis et al. | 205/787 |
| 6,017,696 | A | 1/2000 | Heller | 435/6 |
| 6,093,308 | A | 7/2000 | Lewis et al. | 205/787 |
| 6,099,803 | A | 8/2000 | Ackley et al. | 422/68.1 |
| 6,109,119 | A * | 8/2000 | Jiang et al. | 73/865.5 |
| 6,113,768 | A | 9/2000 | Fuhr et al. | 204/643 |
| 6,129,828 | A | 10/2000 | Sheldon, III et al. | 204/518 |
| 6,224,745 | B1 | 5/2001 | Baltruschat | 205/775 |
| 6,225,059 | B1 | 5/2001 | Ackley et al. | 435/6 |
| 6,287,832 | B1 | 9/2001 | Becker et al. | 435/173.9 |
| 6,294,063 | B1 | 9/2001 | Becker et al. | 204/450 |
| 6,790,330 | B1 * | 9/2004 | Gascoyne et al. | 204/547 |

FOREIGN PATENT DOCUMENTS

| | | | |
|---|---|---|---|
| EP | 0625267 | 11/1994 | |
| EP | 0680380 | 11/1995 | |
| EP | 0691891 | 1/1996 | |
| EP | 0898493 | 3/1999 | |
| GB | 2266153 | 10/1993 | |
| JP | 1-196566 | 8/1989 | |
| JP | 5-126796 | 5/1993 | |
| JP | 6018523 | 1/1994 | |
| SU | 474723 | 6/1975 | 204/643 |
| WO | WO 90/08759 | 8/1990 | |
| WO | WO 91/11262 | 8/1991 | |
| WO | WO 93/16383 | 8/1993 | |
| WO | WO 93/20927 | 10/1993 | |
| WO | WO 94/16821 | 8/1994 | |
| WO | WO 94/22583 | 10/1994 | |
| WO | WO 95/13813 | 5/1995 | |
| WO | WO 96/31282 | 10/1996 | |
| WO | WO 97/34689 | 9/1997 | |
| WO | WO 98/10267 | * 3/1998 | 435/4 |
| WO | WO 99/62622 | 12/1999 | |
| WO | WO 00/69565 | 11/2000 | |

OTHER PUBLICATIONS

Wang et al., "Dielectrphertic manipulation of cells with spiral electrodes," *Biophys. J.*, 72:1887-1899, 1997.

Wang et al., "Dielectrophoretic manipulation of particles," presented at the instituted for electrical engineers industrial application society meeting, Orlando, FL, Oct. 1995.

Wang et al., "Non-uniform spatial distributions of both the magnitude and phase of AC electric fields determine dielectrophoretic forces," *Biochim. Biophys. Acta*, 1243(2): 185-194, 1995.

Wang et al., "Particle dipole—dipole interactions in AC electric fields," *Proc. 16th IEEE: Eng. Med. Biol. Soc.*, 774-775, 1994.

Wang et al., "Relationship of dielectrophoretic and electrorotational behaviour exhibited by polarized particles," *J. Phys. D: Appl. Phys.*, 25:905-912, 1992.

Wang et al., "Separation of polystyrene microbeads using dielectrophetic/gravitational field-flow-fractionation," *Biophysical Journal*, 74:2689-2701, 1998.

Washizu et al., "Molecular dielectrophoresis of biopolymers," *IEEE Trans on Industry App.*, 30(4):835-843, 1994.

Washizu, "Electrostatic actuation of liquid droplets for microreactor applications," *IEEE Transactions on Industry Applications*, 34(4):732-737, 1998.

Yang et al., "Cell separation on microfabricated electrodes using dielectrophoretic/gravitational field-flow fractionation," *Analytical Chem.*, 71(5): 911-918, 1999.

Yeh et al., "Effects of antraquinones of Polygonum cuspidatum on HL-60 cells," *Planta Medica*, 54:413-414, 1988.

Zborowski et al., "Continuous cell separation using novel magnetic quadrupole flow sorter," *J. Mag. & Mag. Materials*, 194:224-230, 1999.

Zhang and Hung, "Sensitization of HER-2/Neu overexpressing non-small cell lung cancer cells to chemotherapeutic drugs by tyrosine kinase inhibitor emodin," *Oncogene*, 12:571-576, 1996.

Zhang et al., "Suppressed transformation and induced differentiation of HER-2/Neu overexpressing breast cancer cells by emodin," *Cancer Res.*, 55:3890-3896, 1995.

Co-pending U.S. Appl. No. 09/883,110 by Peter R.C. Gascoyne et al., filed Jun. 14, 2001.

"Bangor biochip heads for California," EPSRC Home Page: http://www.epsrc.ac.uk/documents/about_epsrc/corporate_publi.../bangor.ht, article printed on Dec. 26, 2000.

"Diagnostic dielectrophoresis-on-a-chip," *Science/Technology*, 77(8):32, 1999. Article printed from http://pubs.acs.org/hotartcl/cenear/99022/7708scitobox2.html on Dec. 26, 2000.

Allsopp et al., "Impedance technique for measuring dielectrophoretic collection of microbiological particles," *J. Phys. D: Appl. Phys.*, 32:1066-1074, 1999.

Arnold and Zimmermann, "Rotation of an isolated cell in a rotating electric field," *Naturwissenschaften* 69 297-300, 1982.

Balachandran et al., "Electrostatic atomization of conducting liquids using AC superimposed on DC fields," *IEEE Transactions on Industry Applications*, 30(4):850-854, 1994.

Becker et al., "Separation of human breast cancer cells from blood by differential dielectric affinity," *Proc. Natl. Acad. Sci. USA*, 92(3):860-864, 1995.

Becker et al., "The removal of human leukaemia cells from blood using interdigitated microelectrodes," *J. Phys. D. Appl. Phys.*, 27:2659-2662, 1994.

Cheng et al., "Preparation and hybridization analysis of DNA/RNA form *E. coli* on microfabricated bioelectronic chips," *Nature Biotechnology*, 16:541-546, 1998.

Davis and Giddings, "Feasibility study of dielectrical field-flow fractionation," *Separation Science and Technology*, 21(9):969-989, 1986.

De Gasperis et al., "Microfluidic cell separation by 2-D dielectrophoresis," *Biomedical Microdevices*, 2:11, 41-49, 1999.

El-Kishky and Gorur, "Electric field and energy computation on wet insulating surfaces," *IEEE Transaction on Dielectrics and Electrical Insulation*, 3(4):587-593, 1996.

El-Kishky and Gorur, "Electric field computation on an insulating surface with discrete water droplets," *IEEE Transactions on Dielectrics and Electrical Insulation*, 3(3): 450-456, 1996.

Fuller et al., "Microfabricated multi-frequency particle impedance characterization system," *Micro Total Analysis System*, 265-268, May 2000.

Galicki et al., "Electrohydrodynamic atomization of dielectric fluids," *Conference on Electrical Insulation and Dielectric Phenomena,* IEEE Annual Report, 365-368, 1996.

Gascoyne et al., "A microfluidic device combining dielectrophoresis and field flow fractionation for particle and cell discrimination," *Proceedings of Solid State Sensor and Actuator Workshop, Hilton Head Supplement,* 37-38, 1998.

Gascoyne et al., "Cell separation by conventional dielectrophoresis combined with field-flow-fractionation," *Abstract,* 40th Annual Meeting of the Biophysical Society, Baltimore, Maryland, P. A333, Tu-Pos412, Feb. 17-21, 1996.

Gascoyne et al., "Dielectrophoretic separation of cancer cells from blood," Presented at the Institute for Electrical Engineers Industrial Application Society meeting, Orlando, FL, Oct. 1995, *IEEE*, 1366-1373, 1995.

Gascoyne et al., "Dielectrophoretic separation of cancer cells from blood," *IEEE Transactions on Industry Applications.*, 33(3):670-678, 1997.

Gascoyne et al., "Dielectrophoretic separation of mammalian cells studied by computerized image analysis," *Meas. Sci. Technol.,* 3:439-445, 1992.

Gascoyne et al., "Manipulations of erythroleukemia cells using travelling electric fields," *Proc. 16th IEEE:Eng. Med. Biol. Soc.,* 772-773, 1994.

Gascoyne et al., "Membrane changes accompanying the induced differentiation of friend murine erythroleukemia cells studied by dielectrophoresis," *Biochim. Biophys. Acta,* 1149:119-126, 1993.

Gascoyne et al., "Numerical analysis of the influence of experimental conditions on the accuracy of dielectric parameters derived from electrorotation measurements," *Bioelectrochem. Bioenerg.,* 36:115-125, 1994.

Gascoyne et al., "Use of dielectrophoretic collection spectra for characterization differences between normal and cancerous cells," *IEEE Trans. Ind. Appl.,* 30:829-834, 1994.

Gawad et al., "Impedance spectroscopy cell analysis in microchannels," *Micro Total Analysis Systems,* 253-255, 2001.

Gawad et al., "Micronarcined impedance spectroscopy flow cytometer for cell analysis and particle sizing," *Lab on a Chip,* 1:76-82, 2001.

Giddings, "Field-flow fractionation: analysis of macromolecular, colloidal, and particulate materials," *Science,* 260:1456-1465, 1993.

Hagendorn et al., "Travelling-wave dielectrophoresis of microparticles," *Electrophoresis,* 13:49-54, 1992.

He et al., "Droplet charge-to-mass ratio measurement in an EHD liquid—liquid extraction system," *IEEE Transactions on Industry Applications,* 32(1):146-154, 1996.

Higashiyama et al., "Behavior of water droplets located on a hydrophobic insulating plate under DC field," *IEEE,* 1808-1813, 1998.

Hoffman and Britt, "Flow-system measurement of a cell impedance properties," *J. Histochemistry and Cytochemistry,* 27:234-240, 1979.

Hoffman et al., "Flow cytometric electronic direct current volume and radiofrequency impedance measurements of single cells and particles," *Cytometry*, 1:377-384, 1981.

Hölzel and Lamprecht, "Dielectric properties of yeast cells as determined by electrorotation," *Biochim. Biophys. Acta* 1104:195-200, 1992.

Hosokawa et al., "Handling of picoliter liquid samples in a Poly(dimethylsiloxane)-based microfluidic device," *Anal. Chem.*, 71:4781-4785, 1999.

Huang et al., "Application of AC electrokinetics for cell characterization and manipulation," *Abstract,* 40th Annual Meeting of the Biophysical Society, Baltimore, Maryland, P. A334, Tu-Pos413, Feb. 17-21, 1996.

Huang et al., "Differences in the AC electrodynamics of viable and non-viable yeast cells determined through combined dielectrophoresis and electrorotation studies," *Phys. Med. Biol.*, 37(7):1499-1517, 1992.

Huang et al., "Electrokinetic behaviour of colloidal particles in travelling electric fields: studies using yeast cells," *J. Phys. D: Appl. Phys.* 26:1528-1535, 1993.

Huang et al., "Electrorotational studies of the cytoplasmic dielectric properties of Friend murine crythroleukaemia cells," *Phys. Med. Biol.*, 40:1789-1806, 1995.

Huang et al., "Introducing dielectrophoresis as a new force field for field-flow fractionation," *Biophys. J.*, 73:1118-1129, 1997.

Huang et al., "The removal of human breast cancer cells from hematopoietic CD34+ stem cells by dielectrophoretic field-flow-fractionation," *J. of Hematotherapy & Stem Cell Research*, 8(5): 481-490, 1999.

Huneiti et al., "Harmonic spraying of conducting liquids employing AC-DC electric fields," *IEEE Transactions on Industry Applications*, 34(2):279-285, 1998.

Jinsart et al., "Inhibition of myosin light chain kinase, cAMP-dependent protein kinase, protein kinase C and of plant CA-dependent protein kinase by antraquinones," *Biological Chemistry*, 373:903-910, 1992.

Jones and Kallio, 'Dielectrophoretic levitation of spheres and shells,' *J. Electrostat.*, 6:207-224, 1979.

Jones, Electromechanics of Particles, Cambridge University Press, Cambridge, Chapter 3:34-82, 1995.

Kashyap and Gratzl, "Electrochemistry in microscopic domains. 1. The electrochemical cell and its voltammetric and amperometric response," *Anal Chem.*, 70:1468-1476, 1998.

Kloes and Koenig, "Basic investigation of the performance of droplets on electrically stressed polymer surfaces," *Conference on Electrical Insulation and Dielectric Phenomena*, IEEE Annual Report, 374-377, 1997.

Lee and Kim, "Liquid micromotor driven by continuous electrowetting," *IEEE*, 538-543, 1998.

Markx and Pethig, "Dielectrophoretic separation of cells: continuous separation," *Biotechnology and Bioengineering*, 45:337-343, 1995.

Markx et al., "Dielectrophoretic characterization and separation of micro-organisms," *Microbiol.*, 140:585-591, 1994.

Massey, "Mechanics of Fluids," 2nd Edition, 136-139, 1975.

Metwally, "Electrostatic charging and modeling of aqueous sprays and fission of droplets," *Conference on Electrical Insulation and Dielectric Phenomena*, IEEE Annual Report, 117-120, 1996.

Mizuno et al., "Behavior of water droplets on silicone rubber sheet under AC voltage application," *IEEE*, 96-99, 1998.

Moesner et al., "Electrostatic devices for particle microhandling," *IEEE Transactions on Industry Applications*, 35(3):530-536, 1999.

Sathuvalli and Bayazitoglu, "The lorentz forces on an electrically conducting sphere in an alternating magnetic field," *IEEE Transactions on Magnetics*, 32(2):386-399, 1996.

Sato et al., "Experimental investigation of droplet formation mechanisms by electrostatic dispersion in a liquid—liquid system," *IEEE Transactions on Industry Applications*, 33 (6):1527-1534, 1997.

Sato et al., "Production of oil/water type uniformly sized droplets using a convergent AC elctric field," *IEEE Transactions on Industry Applications*, 32(1):138-145, 1996.

Vennard, "Elementary Fluid Mechanics," 150-155, 1954.

Wang et al., "A theoretical method of electrical field analysis for dielectrophoretic electrode arrays using Green's theorum," *J. Phys. D: Appl. Phys.*, 29:1649-1660, 1996.

Wang et al., "A Unified theory of dielectrophoresis and travelling wave dielectrophoresis," *J. Phys. D: Appl. Phys.*, 27:1571-1574, 1994.

Wang et al., "Changes in Friend murine erythroleukaemia cell membranes during induced differentiation determined by electrorotation," *Biochimica et Biophysica Acta*, 1193: 330-334, 1994.

Wang et al., "Dielectrophoretic manipulation of cells using spiral electrode arrays," *Abstract*, 40th Annual Meeting of the Biophysical Society, Baltimore, Maryland, p. A333, Tu-Pos411, Feb. 17-21, 1996.

* cited by examiner

TOP VIEW

COMMON ELEMENTS IN FIG.'S A, B AND C BELOW:

SEPARATION CHAMBER ASSEMBLY INCORPORATING ELECTRODES, MAGNETRODES AND FLUID FLOW PATH

ARMATURE TO COUPLE MAGNETIC FIELD TO MAGNETRODE BUSES

ELECTRICAL CURRENT SUPPLY

SOLENOID

SUPERCONDUCTING MAGNET

LIQUID NITROGEN BATH

ARMATURE COUPLING

CONVENTIONAL MAGNET

METHOD AND APPARATUS FOR COMBINED MAGNETOPHORETIC AND DIELECTROPHORETIC MANIPULATION OF ANALYTE MIXTURES

This application claims priority to provisional patent application Ser. No. 60/211,757 filed Jun. 14, 2000, entitled, "Method and Apparatus for Combined Magnetophoretic and Dielectrophoretic Manipulation of Analyte Mixtures" by Peter R. C. Gascoyne, Jody V. Vykoukal, and Frederick F. Becker. The entire text of the above-referenced disclosure, including figures, is specifically incorporated by reference herein without disclaimer.

The following issued U.S. patents are hereby incorporated by reference: U.S. Pat. Nos. 5,858,192, 5,888,370, 5,993,632, and 5,888,370. The following patent applications are hereby incorporated by reference: pending U.S. patent application Ser. No. 09/249,955 for "Method and apparatus for programmable fluidic processing" filed Feb. 12, 1999; pending U.S. patent application Ser. No. 09/395,890 for "Method and apparatus for fractionation using generalized dielectrophoresis and field flow fractionation" filed Sep. 14, 1999; provisional patent application Ser. No. 60/211,515 filed Jun. 14, 2000 for "Dielectrically-Engineered Microparticles" filed Jun. 14, 2000; provisional U.S. patent application Ser. No. 60/211,514 for "Systems and methods for cell subpopulation analysis" filed Jun. 14, 2000; and provisional U.S. patent application Ser. No. 60/211,516 for "Apparatus and method for fluid injection" filed Jun. 14, 2000.

FIELD OF THE INVENTION

The present invention relates to an apparatus and methods for combined magnetophoretic and dielectrophoretic manipulation.

BACKGROUND OF THE INVENTION

One of the most important capabilities that enables the characterization and preparation of bio-materials throughout the life sciences is the recognition of target components in a mixture and the ability to selectively manipulate, interact, and/or isolate them. Methods known in the art to accomplish these steps include magnetic labeling techniques. In these methods, magnetically-susceptible particles (herein termed "magnetic labels" or "labels") are used that can be attracted to a magnet and have modified surfaces that bind preferentially to target particles, cells, or molecules (herein termed "target analytes"). The surface characteristics of the labels that provide for preferential binding can include, but are not restricted to, antibodies, chemically-reactive groups, and receptor ligands. Such surface-modified magnetically-susceptible labels tend to become attached to target analytes to which they have preferential binding capacities within a mixture of analytes.

After attachment, the magnetic labels may be collected by an inhomogeneous magnetic field created by a magnet that is usually equipped with a mechanism for increasing the magnetic field inhomogeneity in the vicinity of the labels. Analytes in the mixture having negligible magnetic susceptibility and that have not become bound to the magnetically susceptible labels to form analyte-label complexes are not collected by the magnet and can be washed away. Subsequently, the magnetic field can be removed and the analyte-label complexes can be released and collected in a separate fraction.

Thus, by using these differential trapping characteristics, current magnetic labeling methods allow target analytes to be isolated from a mixture of particles, cells, or molecules. These magnetic labeling methods can be used to retain the target analytes for further processing, analysis, or study (known in the art as "positive selection"). Alternatively, the analytes that are not retained by the magnetic field may be collected and used for further processing, analysis, or study (known in the art as "negative selection"). While the use of magnetic labeling methods is widespread, current methods have a number of significant disadvantages. For example, because all magnetic labels in a mixture are attracted to the collection magnet regardless of any differences there may be in their surface modification or binding state with target analytes, it is impossible to discriminate between, and isolate, multiple target analytes simultaneously. It is also impossible to determine the extent to which magnetic labels have bound a target analyte without additional measurement steps after magnetic collection. For example, it is impossible to distinguish between or isolate cell subpopulations that are characterized by variations in the number of labels bound to their surfaces since all cells that bind labels, regardless of the number, are collected by current magnetic methods. Finally, current methods depend on trapping the magnetic labels on surfaces in a collection chamber or column and the target analytes tend to be collected in clumps. This typically limits sample recovery because of adhesion to the chamber or column and may entrap unwanted unlabelled analytes within the labeled analytes thereby limiting the purity of the recovered target analytes.

A newer approach to the discrimination, manipulation, separation and isolation of target analytes from a mixture is based on the exploitation of the dielectric properties of the target analytes themselves or the use of dielectric labeling techniques. In U.S. Pat. Nos. 5,993,630 and 5,888,370 which are hereby expressly incorporated herein by reference, certain of the inventors of the present application teach the use of dielectrophoretic methods for the discrimination, separation and isolation of particles by exploiting their intrinsic dielectric properties in conjunction with the characteristics of a hydrodynamic flow profile.

In a concurrently filed provisional patent application concerning dielectric beads for the identification and sorting of target agents, the inventors teach methods by which labels that incorporate useful dielectric and magnetic properties may be designed. Such labels allow target analytes to be discriminated and manipulated by dielectrophoretic methods. By combining magnetic and dielectric properties as useful attributes of the labels, those methods allow for additional levels of discrimination between both the labels themselves and analyte-label complexes. For example, the disclosure teaches how different types of labels may be designed that have distinct "dielectric fingerprints" that allow for the recognition of the different label types within a "cocktail" of different label types. Because analytes, labels or analyte-label complexes do not have to be trapped in a column in order to achieve separations in these dielectric methods, they are less susceptible to entrapping unlabeled analytes within clumps. In addition, all analytes can be kept away from potentially adherent surfaces during dielectric separations so that sample recovery efficiency is improved. Nevertheless, the intrinsic dielectric properties of target particles, cells, or molecules, or of their dielectric labels may still not allow for sufficient discrimination between multiple target analytes in complex mixtures.

Furthermore, the existing dielectric methods having the most discrimination between different analytes (termed Dielectrophoretic Field-Flow Fractionation (DEP-FFF methods) exploit a balance between dielectrophoretic and sedimentation forces on analytes in the sample mixture. Such a balance can only be realized if there is a specific orientation of the apparatus with respect to a gravitational or centrifugal field. This precludes or limits the use of the methods for applications in microgravity environments such as space. The need to attain a balance between dielectrophoretic and sedimentation forces also places constraints on the relative densities of the suspending medium that carries the analyte mixture and the analytes to be separated. For example, the target analyte or, in the case of dielectric labeling, the analyte-label complex, must have a density that is slightly (typically 2–20%) higher than the suspending medium for effective DEP-FFF separation. Finally, because the sedimentation force acting on a target analyte or target analyte-label complex is usually small and uniform in space within the separation chamber, it typically takes many minutes for analytes or analyte-label complexes to reach positions in the dielectric separation apparatus where a balance of forces occurs.

Thus it is often necessary to allow a sample to sit for some "relaxation time" after it is introduced into a DEP-FFF separator to give analytes time to sediment before separation steps are initiated. Since this relaxation time is often comparable to the time taken to complete all of the rest of the separation steps combined, this step significantly slows the separation procedure and is inconvenient.

SUMMARY OF THE INVENTION

To overcome these problems in both magnetic and dielectric separation methodologies, the present invention discloses novel labeling methodology and manipulation procedures in which target analyte-label complexes are subjected to not only magnetic but also dielectric forces simultaneously. The use of two externally applied and controllable forces rather than one introduces versatility for manipulation of the labels and a greatly improved ability to discriminate between analyte-label complexes.

The methods disclosed herein depend upon positioning target analytes to different heights within a hydrodynamic flow profile. Whereas previous methods achieved such positioning through the balance of gravitational and dielectrophoretic forces, the present invention achieves positioning through a balance of dielectric and magnetic forces. Specifically, disclosed herein is a new apparatus and methods that allow dielectrophoresis, magnetopheresis and hydrodynamic effects to be exploited simultaneously for the discrimination, manipulation, fractionation, identification and/or isolation of analytes.

The following objects of the present invention are made possible as a result of this enhancement. First, the methods of the present invention allow several target analytes to be discriminated and isolated simultaneously in a single separation step. Second, target analytes do not have to be collected in the separator and, indeed according to the present invention, can be prevented from contacting any surface to which they may adhere during separation. This not only greatly reduces the problem of trapping of unwanted analytes within target analyte fractions, but also improves analyte recovery efficiencies. Third, apparatus according to the present invention can operate in any orientation, as well as in microgravity environments. Fourth, it is an object of the present invention to obtain discrimination that is much greater than that obtainable by previous methods. Fifth, because both the magnetophoretic (MAP) and dielectrophoretic (DEP) force fields used to position the analyte-label complexes are inhomogeneous in space, the positioning force may be greater than a sedimentation force, thus positioning according to the present invention can occur quicker than in cases where gravitational sedimentation is used. This reduces or eliminates the "relaxation time" prior to separation. Sixth, the present invention introduces improvements that allow bead labeling methodologies to be fully exploited.

DETAILED DESCRIPTION

Figure 1:
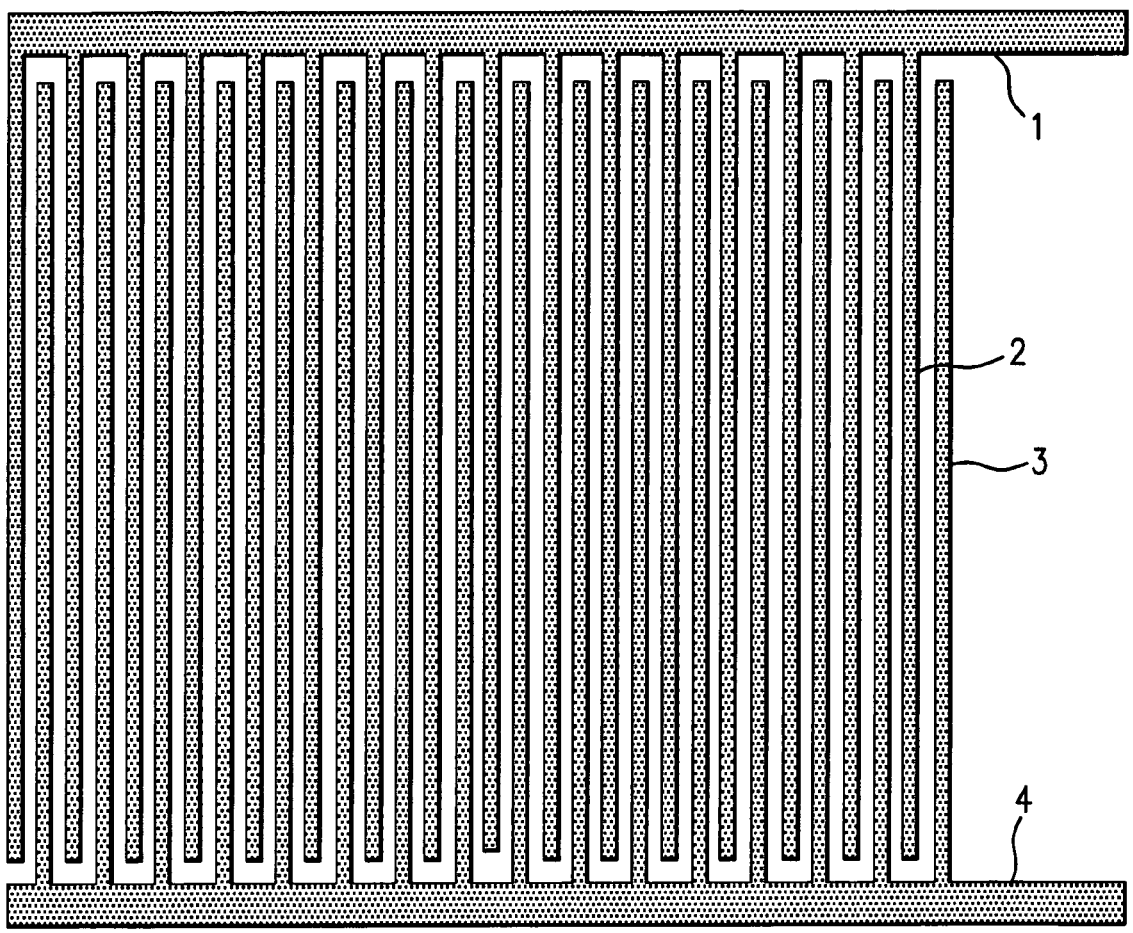
FIG. 1 shows an electrode array including a conductor patterned on a non-conducting substrate, in accordance with embodiments of this disclosure.

To fully understand the new methods it is helpful to introduce the key physical principles that underlie their operation. To accomplish this, dielectrophoretic and magnetophoretic forces are discussed and shown to vary spatially in the vicinity of arrays of electrodes (as used herein, "electrode" means any electric pathway, for example an array of conductors) and magnetrodes (as used herein, "magnetrode" means any magnetic pathway, for example, a strip of paramagnetic material having a high permeability), show the conditions for these forces to be brought into balance when they act on bodies having both dielectric and magnetic susceptibilities, and discuss hydrodynamic flow profiles. Exemplary embodiments and applications will then be given.

1) The Dielectrophoretic Force, $F_{DEP}$

Consider a particle (which may include a solid, cell, virus, bacterium, molecule, or any other localized arrangement of matter that is distinct from and carried within a suspending medium) of volume v and complex permittivity $\epsilon^*_p$ suspended in a medium of real permittivity $\epsilon^*_s$ and complex permittivity $\epsilon^*_s$ that is subjected to simultaneous dielectrophoretic (DEP) and magnetophoretic (MAP) forces. What if these forces are imposed by arrays of electrodes and magnetrodes that give rise to electrical and magnetic field inhomogeneity distributions? Let us further assume that at a given point in space with coordinates x, y, z referred to the electrode/magnetrode coordinates frame, the electric and magnetic fields are E(x, y, z) and H(x, y, z), respectively. (It is to be understood that the magnetic field may also be generated by an array of permanently magnetic elements for the purposes of this disclosure).

According to the dipole approximation, the DEP force is given by:

See equation 1 of Table 1.

Here, R is the radius of the particle, which for simplicity is assumed to be spherical, the $f_{CM}$ factor is the Clausius-Mossotti factor, which reflects the frequency-dependent dielectric polarizability of the particle with respect to its suspending medium, and $\omega_E$ is the frequency of the AC electrical field. It is understood that in the case of non-spherical particles and to describe situations in which quadruple and higher order DEP force components are significant, more complicated expressions than equation (1) will apply as is known in the art (see for example the analysis of higher order poles set forth in X. J. Wang et al).

Further background on dielectrophoretic forces may be found in Thomas B. Jones, "Electromechanics of Particles," Ch. 3 (Cambridge University Press, 1995).

2) The Magnetophoretic Force, $F_{MAP}$

A particle of volume v and magnetic permeability $\mu^*_p$ placed into an inhomogeneous magnetic field will experience a magnetophoretic force See Equation 2 of Table 1

Here, $\mu_s$ is the magnetic permeability of the suspending medium, R is the radius of the particle, and the $k_{cm}$ factor is the magnetic Clausius-Mossotti factor describing the magnetic polarizability of the particle with respect to its suspending medium. Here $\omega_H$ is the frequency of the applied magnetic field and will have the value 0 for a static field. In analogy with the dielectric equation (1), $\mu_s$ and $\mu_p$ are the complex permeabilities of the suspending medium and particle, respectively. In the case of a static magnetic field, these reduce to the real, static magnetic permeability parameters $\mu_s$ and $\mu_p$, respectively.

The inventors note that equation (2) is the magnetic analog of dielectric equation (1). Alternately, if the particle has a permanent volume magnetization m, then the magnetophoretic force will be See Equation 3 of Table 1

It is possible for a particle to have both permanent and inducible magnetic polarization components. In that case a combination of equations (2) and (3) may apply. For example, a particle may have a high permeability and at the same time demonstrate magnetic remnance.

Further background on magneticophoretic forces may be found in Thomas B. Jones, "Electromechanics of Particles," Ch. 3 (Cambridge University Press, 1995).

3) Spatial Variations of Electric and Magnetic Fields

Assume that the inhomogeneous electrical and magnetic fields are created by applying an alternating voltage to an electrode array and a magnetizing force to a magnetrode array. FIG. 1 represents an electrode array comprising a conductor (e.g., 0.5 μm thick layer of gold) patterned on a non-conducting substrate (e.g., glass). While the electrode elements (2 and 3) are parallel, hinging effects create spatially inhomogeneous electrical fields above and below the plane of the electrode elements if an electrical voltage is applied between electrode buses 1 and 4. Analysis of the inhomogeneous electrical field above the electrode plane here, as discussed in X. J. Wang et al. (Exhibit C), reveals that the dielectrophoretic force experienced by a particle placed in this fringing field region will depend upon the distance of the particle from the plane of the electrodes according to the approximate relationship:

See Equation 4 of Table 1

Here $F_{DEP0}$ is a constant for a given applied voltage and given particle properties, h is the distance of the particle from the electrode plane, and $h_{DEP}$ is a constant that depends on the geometry of the electrode array.

A magnetic analog for this also applies. If the electrodes 2 and 3 of FIG. 1 are considered to be magnetrodes (e.g. thin film magnetrodes) instead of electrodes and if a magnet is connected with poles at buses 1 and 4, then a spatially inhomogeneous magnetic field will be created above and below the plane of the thin film magnetic elements. A magnetically susceptible (or permanently magnetic) particle placed in the vicinity of the magnetrode array will experience a magnetophoretic force according to equation (2) (or equation (3)). In analogy with the electrical case, the particle will experience a magnetophoretic force that falls with increasing distance h from the plane of the plane of the magnetic tracks according to the relationship:

See Equation 5 of Table 1 where $h_{MAP}$ is a decay constant. Here $F_{MAP0}$ is a constant for a given strength of the magnet applied between the magnetrode buses 1 and 4 and for given magnetic properties of the particle.

Now consider the case where electrical and magnetic forces are applied simultaneously. Both electrode and magnetrode arrays may be present simultaneously on a supporting substrate. Further, the geometric characteristics of the electrode and magnetrode arrays may be similar or dissimilar. When geometrical dissimilarity exists, or other prevailing conditions act to distort the magnetic or electric field with respect to one another, the value of the parameters $h_{DEP}$ and $h_{MAP}$ will differ from one another and the electrical and magnetic forces acting on a particle will exhibit different dependencies on the particle distance from the plane of the electrodes and magnetrodes.

While magnetophoretic forces are usually positive (i.e. attractive) in sign in biological labeling applications, conditions may be chosen to make the dielectrophoretic forces negative in such applications. In this case it is possible for the dielectrophoretic and magnetic forces acting on a particle to oppose one another. If $h_{DEP} < h_{MAP}$ in equations (4) and (5), then it is possible to find a unique value for the distance h from the electrode and magnetrode plane where the forces balance, using equations (1) and (2) as:

See Equation 6 of Table 1 where $G_{DEP}$ and $G_{MAP}$ are geometrical functions relating to the spatial characteristics of the electrode and magnetrode elements, $V_0$ is the voltage applied to the electrode buses, and $B_0$ is the magnetic field applied to the magnetrode buses.

This equation reveals that a particle will come to an equilibrium at a height h from the plane of the electrodes and magnetrodes (assuming these elements are coplanar) when:

See Equation 7 of Table 1 giving h=See Equation 8 of Table 1

Alternately, if the particles have a permanent magnetic moment or their magnetic moment has reached a saturation value, then the magnetophoretic force described in equation (3) will fall according to relationship (5) and the decay constant $h_{MAP}$ in Equation 8A of Table 1 will differ from the dielectrophoretic decay constant $h_{DEP}$, even if the geometry of the electrode and magnetrode arrays are identical. In this case, equilibrium height is attained when:

See Equation 9 of Table 1 giving h=See Equation 10 of Table 1

In this case the dielectrophoretic and magnetophoretic fields can be generated from a spatially coincident electrode-magnetrode structure. Note also in this case that while the dielectrophoretic force depends on the square of the applied voltage, the magnetic force depends linearly on the applied magnetic field. It is assumed in equation (10) that the magnetic field, of the magnetic particle remains aligned with the magnetic field from the magnetrode array. If magnetic particles are unable to fully align in this way with the applied magnetic field, then the magnetophoretic force will be smaller than that given by equation (3), as is known in the art. Note also that the height at which DEP and MAP forces balance will be described by an alternative set of equations if the magnetrodes and electrodes are not coplanar and that alternative equations may be derived to describe the dielectrophoretic and magnetophoretic forces for other configurations of electrodes and magnetic elements. This disclosure is intended to cover all such cases and the above equations are meant to be for illustrative purposes in teaching the art.

4) Hyperlayer Field Flow Fractionation

A fluid moving under a laminar flow regime through a thin channel assumes a hydrodynamic flow profile whereby the velocity of the fluid increases with distance from the channel walls up to a maximum velocity at the center of the channel. If the flow profile is parabolic, for example, then the velocity is given by See Equation 11 of Table 1 where h is the distance from the channel wall, D is the height of the channel, and <v> is the mean velocity of the fluid in the channel.

The method of field-flow fractionation (FFF) depends upon positioning particles within a hydrodynamic flow profile by one or more applied force fields which differentially affect particles having different physical properties. Particles positioned at different heights in a flow profile through the influence of the force fields are carried by the fluid at different speeds and are thereby separated.

The present invention discloses methods by which the positions of particles to be separated are controlled within a hydrodynamic flow profile by balancing opposing dielectrophoretic and magnetic forces. It is understood, however, that gravitational forces may also act on the particles and affect their positions or velocities in the hydrodynamic flow profile. In such cases, a combination of gravitational, electric and magnetic forces will determine particle positions and velocities. The effect and use of gravity in DEP-FFF applications has been described in U.S. Pat. Nos. 5,993,630 and 5,888,370 already incorporated herein by reference.

To exploit DEP and MAP forces for positioning particles, a channel is utilized that incorporates electrodes and magnetrodes (or permanently magnetic elements) that generate inhomogeneous electric and magnetic fields within the channel. These fields create dielectrophoretic and magnetophoretic forces on particles within a carrier fluid introduced into the channel. The position of the particles with respect to the channel is influenced by these forces. If the carrier fluid flows through the channel, then the velocity of the fluid at a given position in the channel will depend upon that position, and the velocity with which a particle will be carried by the fluid will therefore be influenced by the effect of the dielectrophoretic and magnetophoretic forces on the particle position.

Figure 2A:
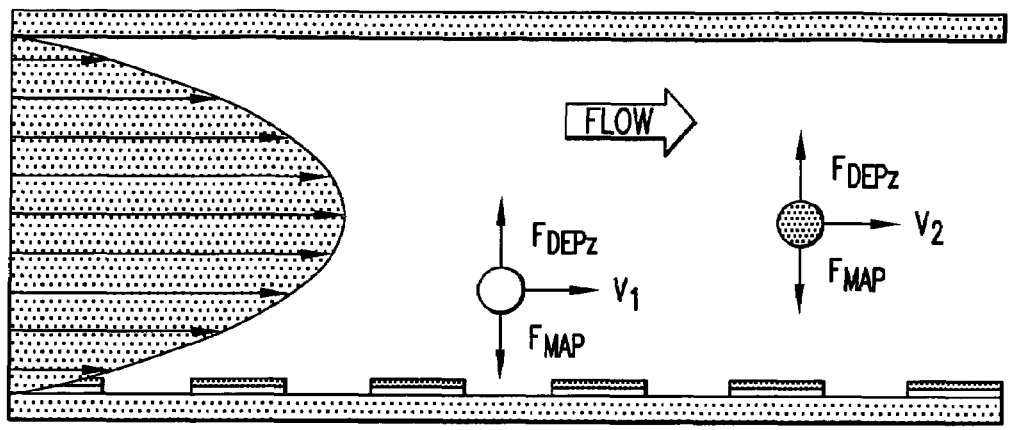
FIG. 2A shows MAP and DEP forces acting on a particle and a hydrodynamic flow profile, in accordance with embodiments of this disclosure.
Figure 2B:
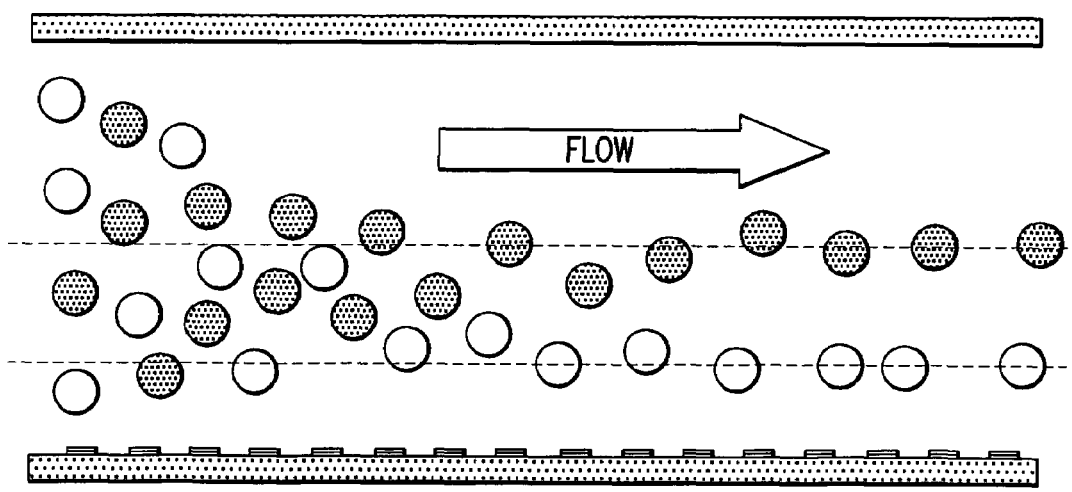
FIG. 2B shows the movement of particles to characteristic heights, in accordance with embodiments of this disclosure.
Figure 3A:
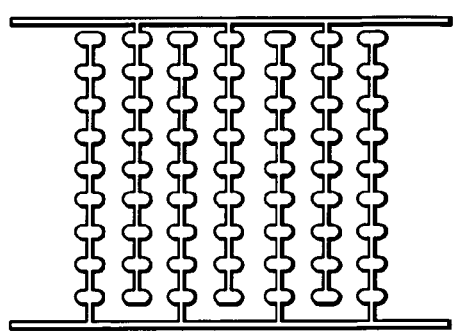
FIGS. 3A–3E show exemplary magnetrode arrays for magnetophoretic manipulations, in accordance with embodiments of this disclosure.
Figure 3B:
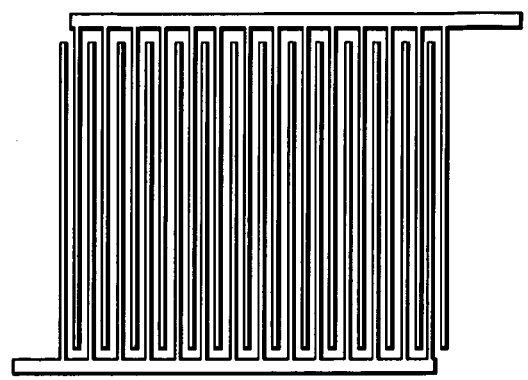
Figure 3C:
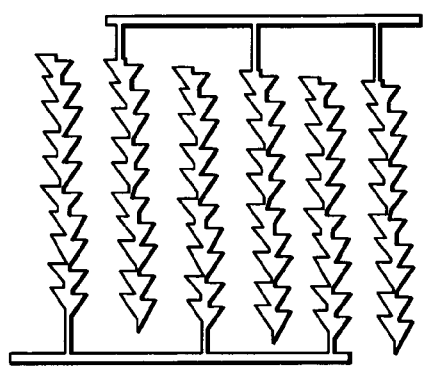
Figure 3D:
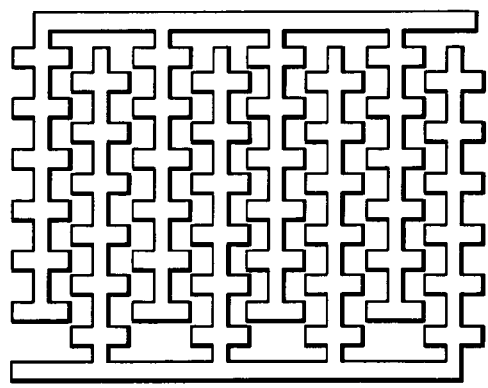
Figure 3E:
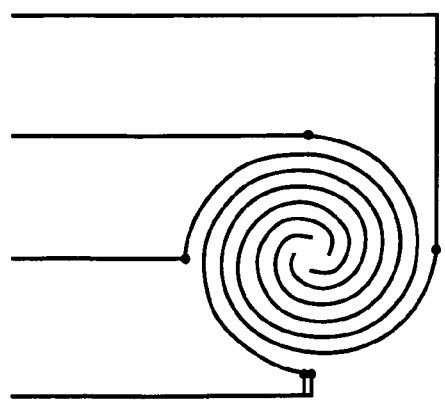

For example, if a given particle is susceptible to both magnetic and dielectric forces, its height may be controlled by the balance of dielectrophoretic and magnetophoretic forces according to equation (8) or equation (10) and the fluid will carry the particle at a velocity given by equation (11). The MAP and DEP forces acting on a particle 18 and the hydrodynamic flow profile 16 are shown in FIG. 2A. As shown in FIG. 2A, the dielectrophoretic force 10 opposes the magnetophoretic force 12. Flow arrow 14 shows the direction of fluid flow within the chamber 20. Further shown in FIG. 2A, is the hydrodynamic profile 16, which in the exemplary embodiment is a parabolic flow profile. Also shown in the exemplary embodiment of FIG. 2A are electrode elements 22 and magnetic elements 24. The movement of particles to characteristic heights is represented in FIG. 2B, in which the fluid flows slowly from left to right. In practice, larger or similar smaller differences in characteristic heights than those shown in FIG. 2B may be exploited for analyte discrimination and separation.

Particles possessing similar physical properties will all be positioned at the same characteristic height in the flow channel and therefore be transported by the fluid at the same rate. Particles having different physical properties will be positioned at different characteristic heights where the fluid flow velocity is different. Therefore, they will be transported through the chamber at different rates. Using this principle, the fractionation of a mixture of different particle types can be accomplished. For example, if a sample containing a particle mixture is introduced at one end of such a flow chamber and carried through the chamber by fluid flow, then different particle types will be carried at different velocities and emerge from the outlet end of the flow chamber at different times where they may be collected in separate fractions. The time taken for a given particle to travel from the inlet to the outlet end of the flow channel is known in the art as its "retention time". The present invention concerns the combination of dielectrophoretic, magnetophoretic and hydrodynamic principles to control the positions and/or retention times of particles in a channel for the purposes of fractionation, separation, isolation, identification and characterization of analytes.

Dielectric and Magnetic Properties of Particles

The factors influencing the dielectric and magnetic properties of particles are well known in the art. In the case where the particle is comprised of an analyte-label complex, it should be appreciated that the properties of the complex will, in general, differ from those of an uncomplexed analyte or an uncomplexed label. This has important implications for the discriminating ability of the invention disclosed herein. Specifically, it should be recognized that the association of a magnetic label with a non-magnetic analyte will result in a magnetic analyte-label complex that has dielectric properties that differ from those of either the label or the analyte, and magnetic properties that differ from those of the analyte.

In general, the label and analyte will contribute dielectric and magnetic properties to the complex that depend on their relative permittivities, permeabilities, volumes, and influences on the charge distributions of the suspending medium. Because the separations describe herein depend upon a balance of dielectrophoretic and magnetophoretic forces, analyte-label complexes will therefore usually exhibit elution characteristics in a DEP-MAP separator that differ from those of labels having no associated analytes.

The methods according to the present invention therefore allow labels to be discriminated and separated according to their association state with respect to analytes. For example, cells that have bound different numbers of magnetic labels will exhibit different characteristics during separation, allowing for their discrimination, characterization, and isolation. Therefore, cells having fewer binding sites for antibodies against EGF receptors may be separated from cells having a greater number of receptors, for example. As another example, labels that are uncomplexed can be separated from labels that are associated with cells, particles, molecules and other target analytes.

In addition, "cocktails" consisting of different types of labels may be produced in which each type of label has a different dielectric and magnetic "fingerprint". Each type of label in the mixture may then be independently discriminated, separated, identified, and characterized according to its respective binding state with a different target analyte. Such cocktails of labels allow for the simultaneous analysis of multiple analyte targets within a mixture in a single separation step.

Influence of Gravity

FIG. 2A shows the MAP and DEP forces acting on particles within a separator and acting to position particles at equilibrium positions (FIG. 2B). It is to be understood when separations are conducted in a gravitational field, as they are on earth, that a force of gravity will also act on the particles. The magnitude of this force acting on a particle is $F_{sediment} = v_g(d_p - d_s)$, where v is the particle volume, $d_p$ is its density, and $d_s$ is the density of the suspending medium. The direction of the gravitational force with respect to the force diagram in FIG. 2A will depend upon the orientation of the separator embodiment with respect to the earth's gravitational field. If the gravitational force has a component in the same direction as $F_{MAP}$ or $F_{DEPz}$, then it will also tend to influence the position of the particle. Therefore, equations (8) and (10) may, in practice, need to be modified by the addition of a gravitational force term. In addition, if the gravitational force has a component that acts in or against the direction of fluid flow in FIG. 9A, then the velocity of the particle given by equation (11) will be modified by the addition of a sedimentation velocity term. For example, if the gravitational force acts in the direction of flow, the additional sedimentation velocity component given, by Stoke's law, as $$v_{sed} = \frac{1}{6} \frac{\tau(d_p - d_s)g}{\eta}.$$

It is to be understood that these gravitational effects may be eliminated by appropriate alignment of the separation apparatus with respect to the gravitational field, or that they may be exploited in order to take advantage of density characteristics of the labels, analytes or analyte-label complexes.

Finally, it should be noted that the electrical fields used to provide the DEP force are easily switchable and may be customized to particular applications and programmed during separations to achieve specific desired types of discrimination. The process of changing the field over time during separation is called programming. Use of programmability to improve DEP-FFF separations is described in pending U.S. patent application Ser. No. 09/249,955, which is expressly incorporated herein by reference. It is to be understood that the magnetic field may also be programmed to further enhance the flexibility, discrimination and capabilities of the invention disclosed herein.

EXEMPLARY EMBODIMENTS

Two exemplary embodiments of separators are described that exploit analyte positioning by a combination of dielectrophoretic and magnetophoretic forces. In the first embodiment, which does not exploit the flow velocity profile of the carrier fluid and is suitable for continuous processing of samples, analyte mixtures may be flowed continuously through a chamber equipped with arrays of electrodes and magnetrodes. Analytes are then subjected to the combined dielectrophoretic and magnetophoretic forces resulting from the electric and magnetic fields. Providing they spend sufficient time within the flow channels, these forces move analytes sufficiently close to characteristic positions in the carrier medium flow profile stream at which the DEP and MAP forces balance so that they may be identified, separated, or isolated. Therefore, analytes emerge from the flow channel at positions that depend on their dielectric and magnetic characteristics. Different analytes may be characterized or separated according to the positions, with respect to the flow channel walls, at which they exit the flow channel by use of an appropriate arrangement of exit ports.

In the second type of embodiment, in which the flow velocity profile of the carrier fluid is exploited and which is best suited to batch processing of samples, a similar apparatus and mode of operation is employed, except that the sample analyte mixture is injected as a single sample that is usually much smaller in volume than the separation chamber. This aliquot is then carried through the flow channel by a carrier medium. Again, provided they spend sufficient time in the DEP and MAP fields, analytes move sufficiently close to positions in the carrier fluid flow profile where the DEP and MAP forces acting on them are balanced so that they may be discriminated or separated. Because the analytes are then carried at different speeds according to their positions in the carrier medium flow profile, they emerge from the flow channel at different characteristic times. It should be understood that a "sufficient time", as used above, means that analytes, labels and analyte-label complexes spend enough time in the MAP and DEP force fields to move to positions at which they may usefully be discriminated, detected, or separated. In practice, this may be less than the time taken for them to come to positions where the MAP and DEP forces exactly balance.

Specific aspects of the apparatus for the two embodiments will now be described. Except for the exit ports, which must be multiple to achieve separation and isolation of analytes for the continuous mode embodiment, other aspects of the two embodiments may be identical. However, it is to be understood that the embodiment having multiple outlet ports may also be operated in batch mode.

Exemplary electrode arrays for dielectrophoretic manipulations are shown in FIGS. 2 and 3. These are planar arrays consisting of a thin film of conductor, such as gold or the like, patterned onto a supporting substrate, such as glass or the like. These arrays may be fabricated by known photolithographic and ebeam patterning techniques. Electrode arrays like these, or of different forms, may be used to provide DEP forces in the separators disclosed herein. Electrodes may be electroplated, printed, etched or affixed to the chamber walls, or otherwise positioned in or around the flow channel to create an inhomogeneous electrical field in the flow channel when they are connected to a signal generator.

Exemplary magnetrode arrays for magnetophoretic manipulations may have similar or different patterns to those shown in FIG. 3. In the magnetic case, the magnetrodes may consist of thin film metals, alloys, or magnetically susceptible materials such as magnetic ceramics or ferrites, magnetically susceptible wires, or strips, wires or other arrangements of permanently magnetic material. These may be attached to the chamber walls or positioned in any location at which they result in the ability to provide an inhomogeneous electrical field within the flow channel.

Figure 4A:
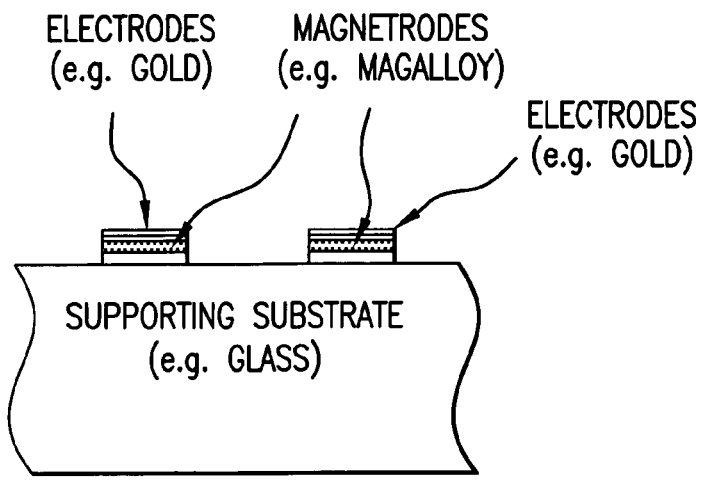
FIGS. 4A–4C show exemplary electrode and magnetrode combinations suitable for simultaneously providing magnetic and electric fields, in accordance with embodiments of this disclosure.
Figure 4B:
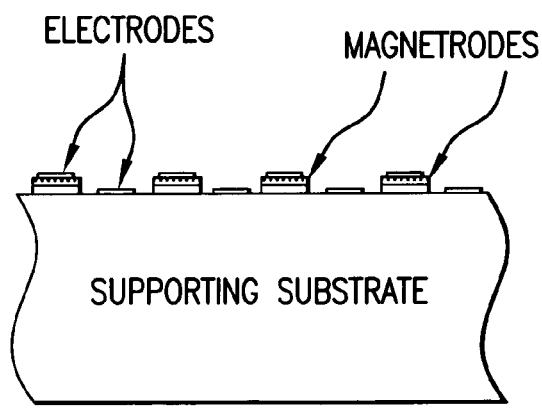
Figure 4C:
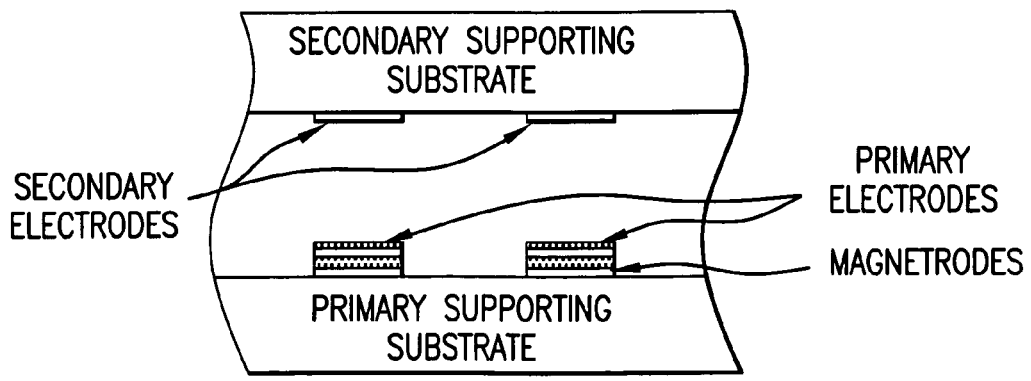
Figure 5A:
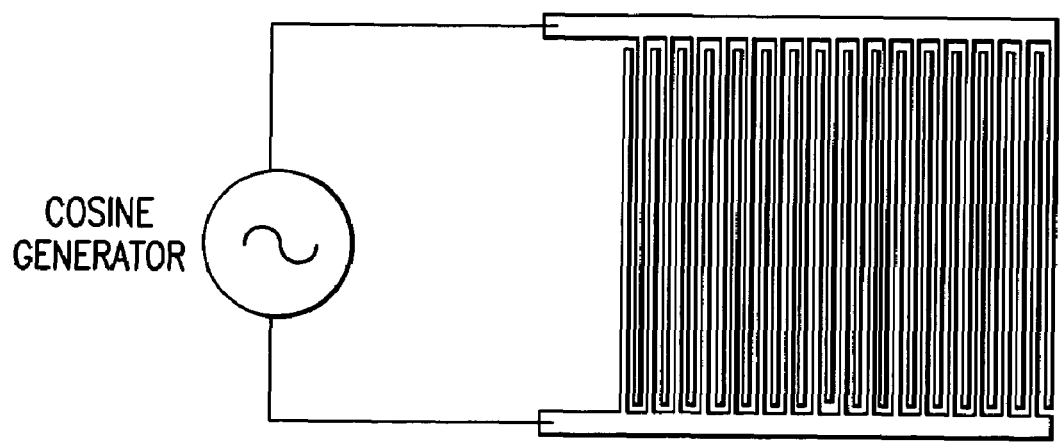
FIGS. 5A–5B show exemplary electrical excitation schemes, in accordance with embodiments of this disclosure.
Figure 5B:
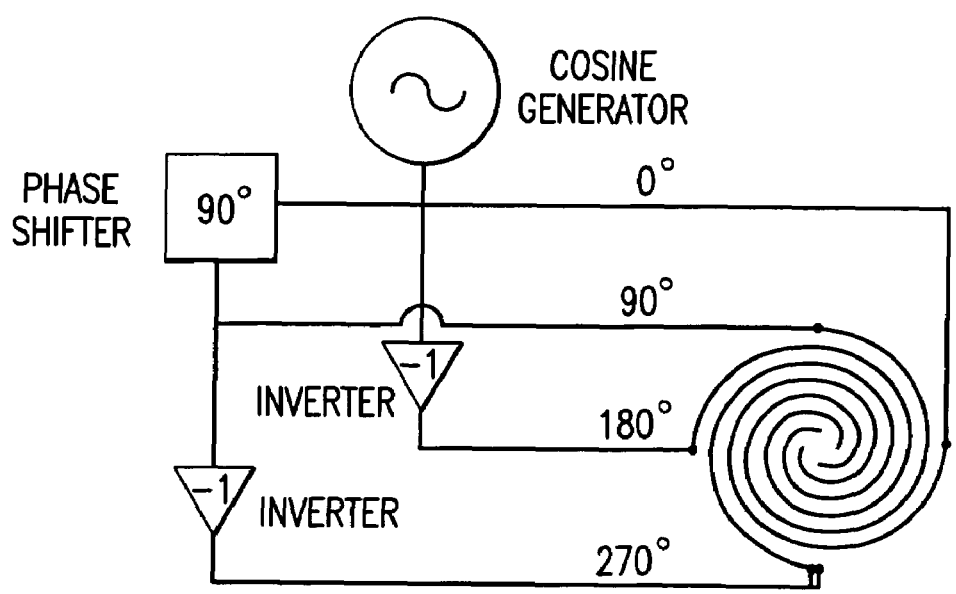

Exemplary electrode and magnetrode combinations suitable for simultaneously providing magnetic and electric fields are shown in cross-section in FIGS. 4A–C. FIG. 4A shows an exemplary structure in which the electrode and magnetrode elements are combined. Specifically, FIG. 4A shows electrodes 22 disposed above magnetrodes 24, which is disposed on structure 26. In alternate embodiments, the magnetrodes 24 may be placed above electrodes 22. Such a structure may be, for example, lithographically patterned from a single photo mask. More complex patterning schemes in which the geometry of the magnetrode and electrode elements differ may be fabricated using two or more patterning masks for photolithography as shown in the example FIG. 4B. As shown in FIG. 4B, the electrode elements 22 are located adjacent the magnetic elements 24. Other methods known in the art may be used to create electrode and magnetrode arrays. It is understood that an additional electrode or electrode array may be incorporated elsewhere in the chamber as illustrated, for example, in FIG. 4C. As shown in FIG. 4C, in addition to the primary electrode structure 22, a secondary electrode structure 28 is disposed on an opposing substrate 30. In exemplary embodiments, the secondary electrode structure 30 may be the same thickness and width as the primary electrode structure 22, or it may be of different size. Exemplary electrical excitation schemes are shown in FIG. 5.

Figure 6A:
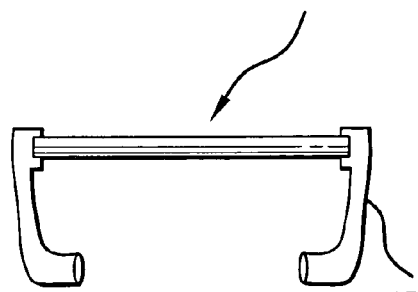
FIGS. 6A–6C show exemplary magnetic field excitation schemes, in accordance with embodiments of this disclosure.
Figure 6A:
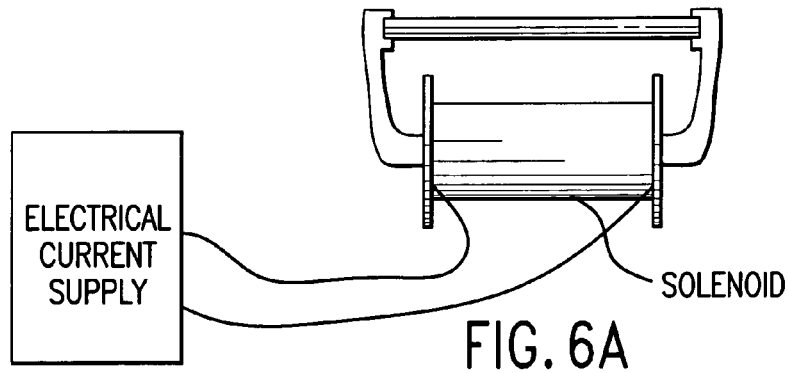
Figure 6B:
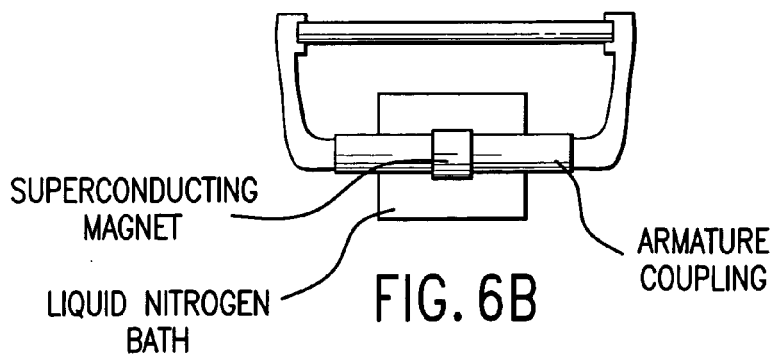
Figure 6C:
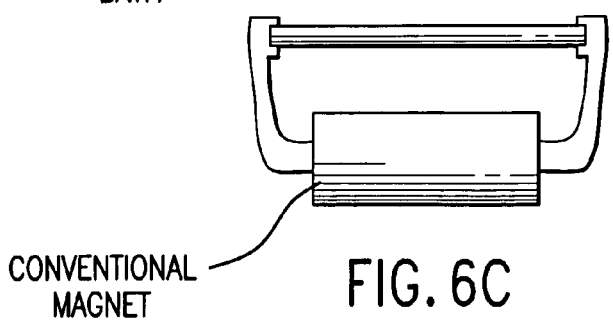
Figure 7A:
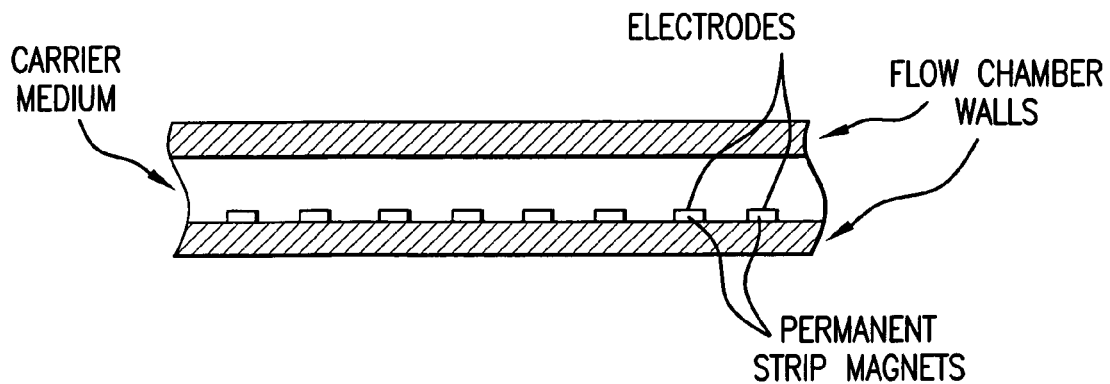
FIG. 7A shows magnetic materials that provide a magnetic field in a flow channel without the need for an external magnet, in accordance with embodiments of this disclosure.
Figure 7B:
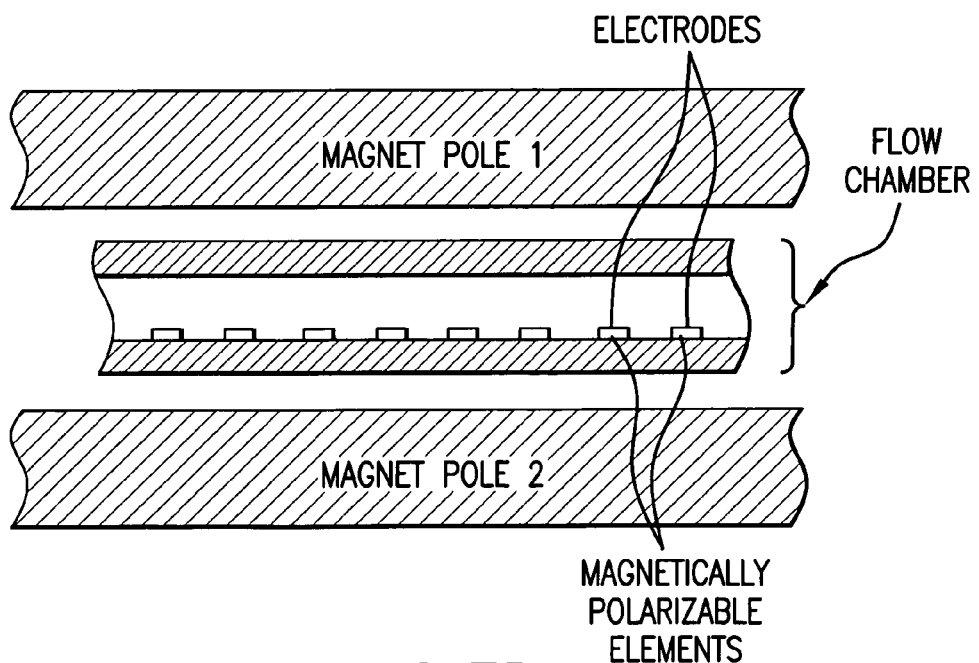
FIG. 7B shows how an array of magnetrodes may be used to introduce inhomogeneity in a magnetic field derived from magnetic poles placed outside the chamber, without the need for a magnetrode pathway to the array, in accordance with embodiments of this disclosure.

Exemplary magnetic field excitation schemes are shown in FIG. 6. Arrays of permanently magnetic materials taking the forms shown in FIG. 2 or any other form may also be used to provide the magnetic field in the flow channel without the need for a external magnet (FIG. 7A). An array of magnetrodes may also be used to introduce inhomogeneity in a magnetic field derived from magnetic poles placed outside the chamber without the need for a magnetrode pathway to the array as shown in FIG. 7B.

Figure 8:
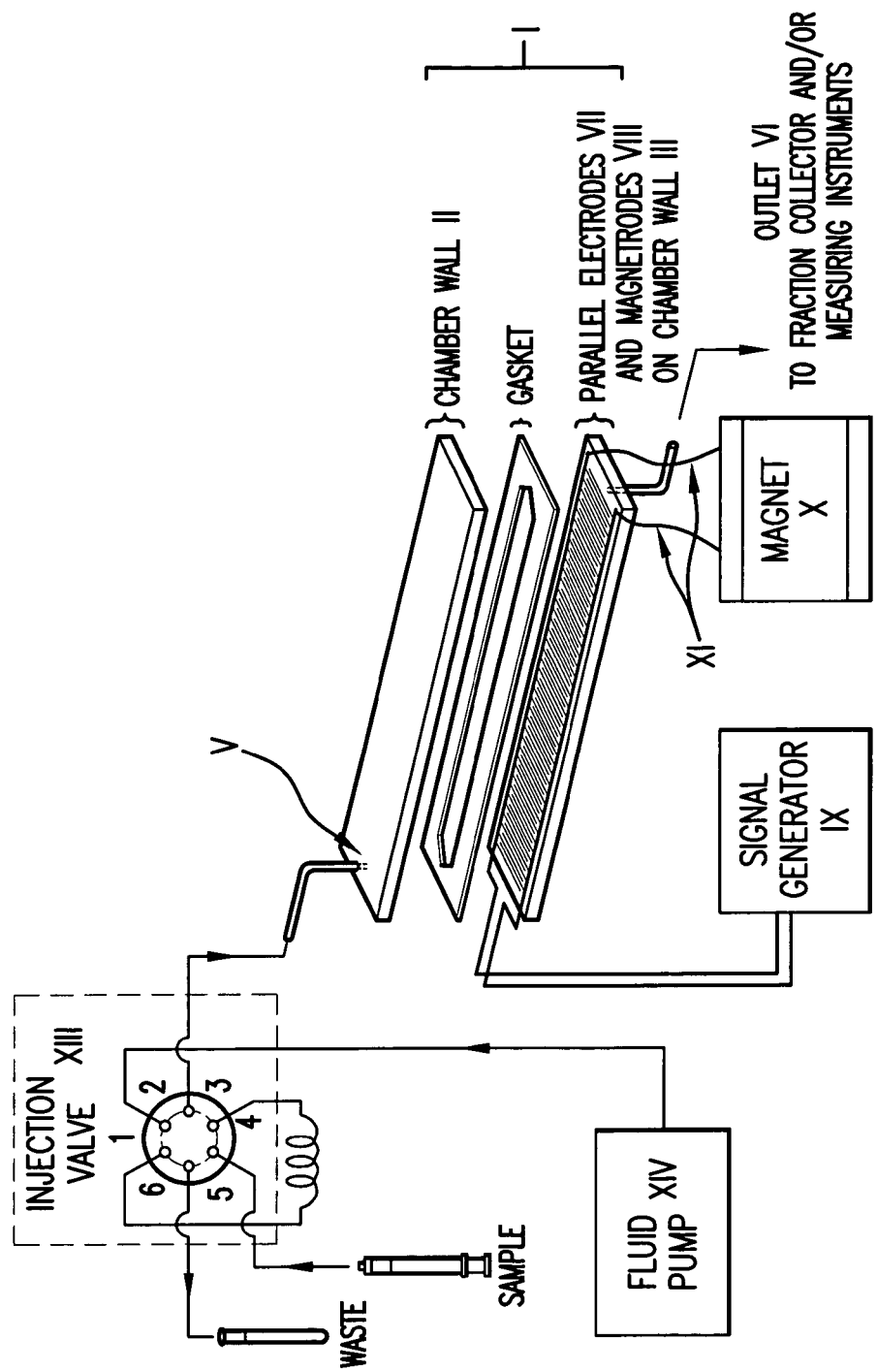
FIG. 8 shows an exemplary embodiment of a separator using the dielectric and magnetic separation principle for batch mode separation, in accordance with embodiments of this disclosure.

An exemplary embodiment of a separator using the dielectric and magnetic separation principle for batch mode separation is shown in enlarged form in FIG. 8. FIG. 8 shows an enlarged view of a thin chamber I comprised of two sidewalls II and III that sandwich a gasket III into which a slot IV has been cut. When assembled, the chamber is tightly held together by clamping and/or gluing, for example, in such a manner that the gasket slot becomes the flow channel.

An entry port V and exit port VI allow for ingress and regress of carrier fluid and sample. In practice there may be multiple ports V and VI.

In alternate embodiments, the flow channel may be derived from a slot cut directly into one or both of the side walls by etching, machining, ablation, lithographic means, or by any other procedures known in the art. Alternately, the flow channel may be derived from material that is applied to one or both side walls by sputtering, spin coating, printing or thin film deposition, may be cut or formed into the body of the device, or may be injection molded, produced by any other procedures known in the art.

Arrays of electrodes VII and magnetrodes VIII are present in the flow channel. These may be within the channel interior itself, be supported by one or more walls of the chamber, or be outside the chamber. Electrical signals are connected from a single generator IX. A magnetic field is provided from magnet X via buses XI and XII to the electrodes and magnetrodes, respectively.

Figure 9A:
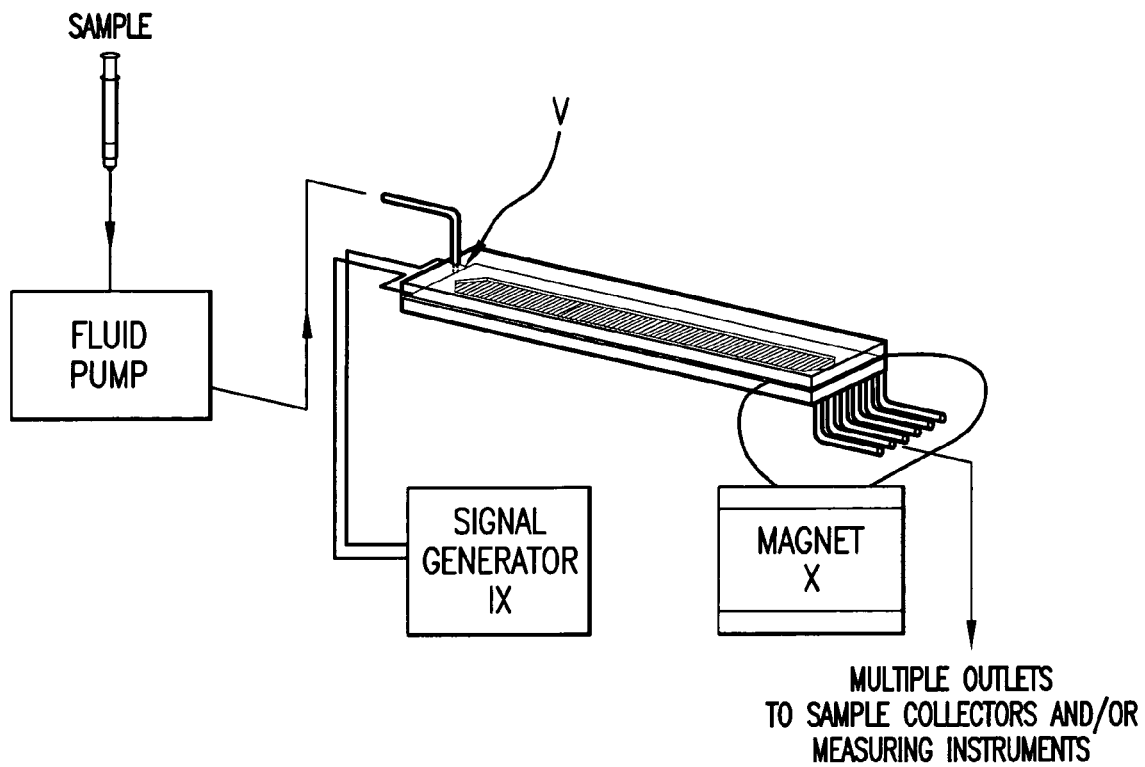
FIGS. 9A–9B show continuous mode separation, in accordance with embodiments of this disclosure. The outlet port arrangement comprises multiple ports configured so as to collect bands of fluid that travel through the flow chamber at certain defined distances from the electrode and magnetrode elements and from the walls of the flow chamber.
Figure 9B:
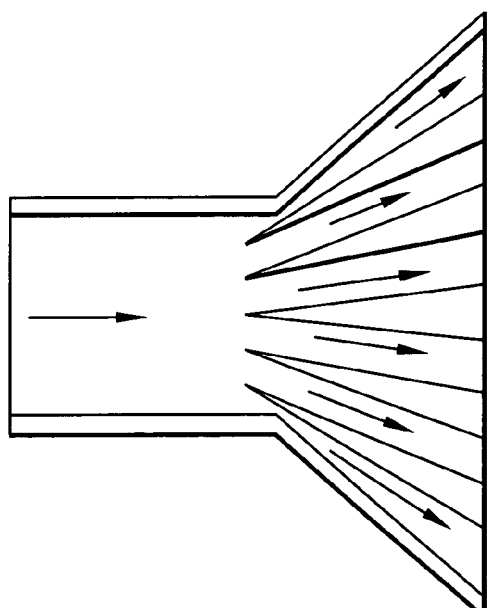

A second embodiment for continuous mode separation is shown in FIG. 9. FIG. 9 shows an alternate embodiment wherein all elements of the diagram with the exception of the outlet port VI are the same as described in FIG. 8. In FIG. 9, the outlet port arrangement comprises multiple ports configured so as to collect bands of fluid that travel through the flow chamber at certain defined distances from the electrode and magnetrode elements and from the walls of the flow chamber. Specifically, FIG. 9a shows how carrier fluid traveling through the flow channel at different distances from the flow channel walls can be removed from the flow channel through, for example, six exit ports. Analytes or labels or analyte-label complexes carried in the carrier medium at different distances from the chamber floor, at bottom of the diagram, are thereby caused to exit through different exit ports.

Description of batch-mode operation

In an exemplary separation using the batch mode, the following steps are ufndertaken:

(1) A sample containing one or more analytes is mixed with labels having dielectric and magnetic properties and binding affinity to one or more types of target analyte. If desired, labels having distinguishable magnetic and dielectric properties and binding affinities for different analytes may be used in combination in this step.

(2) After an incubation period that is sufficient to ensure adequate binding between target analytes and labels, a measured aliquot of the analyte/label mixture is injected into the inlet end of the separation channel.

(3) Magnetic and AC electrical fields are applied to the magnetrode/electrode arrays in the separation channel. This step may precede or follow the sample injection step.

(4) Following a suitable relaxation time during which analytes and analyte-label complexes approach sufficiently close to positions with respect to the electrode and magnetrode arrays where the MAP and DEP forces balance, flow of carrier medium is initiated at the inlet end of the separation channel.

(5) The carrier medium establishes a hydrodynamic flow profile within the separation channel and carries analytes and analyte-label complexes through the separation channel at velocities depending on their positions with respect to the channel walls. This position depends upon the applied magnetic and AC electrical fields and may, in exemplary embodiments, be influenced by the hydrodynamic flow profile and by gravity.

(6) Different analytes and analyte-label complexes will emerge from the outlet end of the chamber at different times and may be collected in separate fractions or detected by various measurement methods. Because analyte-label complexes having similar magnetic and dielectric properties will be positioned similarly by the synergistic action of the magnetic and dielectric forces acting in the separation channel, they will be carried at similar velocities by the carrier medium and will emerge together at the channel outlet in a single elution peak. In contrast, analytes and analyte-label complexes having different properties will be differentially positioned by the synergistic action of the magnetic and electric fields, will be carried at different velocities by the carrier medium, and will emerge from the channel outlet at different times. In this way, a mixture of analytes may be discriminated and separated temporally into several characteristic peaks or bands. Either of the exemplary embodiments may be operated in batch mode.

DESCRIPTION OF CONTINUOUS MODE OPERATION (1) A sample containing one or more analytes is mixed with labels having dielectric and magnetic properties and binding affinity to one or more types of target analyte. If desired, labels having distinguishable magnetic and dielectric properties and binding affinities for different analytes may be used in combination in this step. The mixture is allowed to incubate for sufficient time that adequate binding between target analytes and labels occurs.

(2) Magnetic and AC electric fields are applied to the magnetrode and electrode arrays in the separator channel.

(3) The analyte/label mixture from (1) is continuously injected into the inlet port of the flow channel.

(4) Carrier medium is withdrawn from multiple exit ports of the separator (see FIG. 9). Different analyte fractions emerge from each port.

In this way a mixture of analytes and analyte-label complexes may be continuously separated into fractions that emerge from different exit ports.

Release of Magnetic Particles by Dielectrophoretic Forces

The invention disclosed herein describes methods for analyte, label and analyte-label complex discrimination that depend upon an interaction (specifically a balance) of MAP and DEP forces.

DEP forces may also be used to overcome a common problem associated with permanent magnets in magnetic labeling applications. Specifically, current magnetic separation technologies depend upon the ability to remove the magnetic field in order to release the magnetic labels and analyte-label complexes after they have been collected. Magnetic separations are normally accomplished by using a separation chamber or separation column to which a magnetic field is applied by exterior means, such as a permanent magnet or an electromagnet. After collection of the magnetic labels and analyte-label complexes, the separation chamber or column must be removed from the vicinity of the permanent magnet, or the electromagnet turned off, so that the labels and label-analyte complexes are released. This requirement to remove the magnetic field in order to release the collected analytes precludes the use of permanent magnets or arrays of permanent magnets that are located within the separation chamber itself.

The present invention allows this limitation to be overcome. This is because apparatus according to the present invention allow for the magnetic labels and label-analyte complexes to be repelled from the magnetic elements in the collection chamber by DEP forces. For example, FIG. 6A shows a separation chamber having an integral array of permanent magnets.

Elsewhere in this specification, it is assumed that the DEP force is sufficient to prevent attachment of the magnetic labels and analyte-label complexes to the magnetrodes or permanent magnetic elements. However, in an alternate mode of operation, the DEP force is switched off or kept at a low level while the magnetic field is present. In the absent of a counterbalancing DEP force, the magnetic labels and analyte-label complexes are attracted to, approach, and contact the magnetic elements and become immobilized on them. In this mode of operation, the separation chamber therefore initially functions like a conventional magnetic separation chamber or column and retains the labels and analyte-label complexes from the suspending medium.

After collection, however, the DEP force is switched to a sufficiently high level to repel and dissociate the collected magnetic labels and analyte-label complexes from the magnetic elements without the need to remove the magnetic field. It should be noted that the dissociation of the magnetically collected species by the DEP force by raising the voltage applied to the electrode array from a small to a high volume over a period of time, different labels and analyte-label complexes may be released at different times and may be flushed from the separation chamber and collected in different fractions.

This mode of operation allows permanent magnetic elements to be incorporated into separation chambers, a feature that is especially useful in microfluidic embodiments. By allowing the incorporation of permanent magnet elements, the need for more powerful external magnets is eliminated. Alternately, by eliminating the need to remove the magnetic field, fixed external magnets may be used if desired.

Exemplary Applications

Using apparatus and methods according to the present invention, various matter may be magnetized. Particularly, with the present invention, discrimination, separation, identification, detection, manipulation and isolation of the following matter may be accomplished:

(a) cell subpopulations including, for example:

blood cells in accordance with their antibody and dielectric profiles (such as CD34+, CD8+, CD4+, CD14+, CD18+, CD5+, etc.);

rare cells from blood such metastatic cells (such as EGF+, CD5+, epithelial marker+, etc.);

target cells from needle biopsies;

nucleated fetal cells from maternal fluids (such as erythrocytes from maternal blood, chord blood, amniotic fluid, etc.);

gram negative from gram positive bacteria;

parasites and parasitized cells, such as malaria, from body fluids and normal cells;

bacteria from blood, urine, saliva, amniotic fluid, needle biopsies;

(b) mycoplasma, fungal, and viral particles subpopulations including those from blood, urine, saliva, amniotic fluid, needle biopsies;

(c) potentially pathogenic cells, viral particles, mycoplasma, fungal spores, bacterial spores from the environment for water analysis in public health maintaining food processing plants, food distribution, restaurants, homes, biowarefare, bioterrorism detection.

(d) molecular subpopulations including proteins (such as in diagnostics and prognostics, separations for biotechnology, research, pharmaceuticals);

nucleic acids (such as in diagnostics and prognostics, biotechnology, gene therapy, research, pharmaceuticals);

lipids (such as in diagnostics and prognostics, biotechnology, gene therapy, research, pharmaceuticals)

complex molecules (such as in diagnostics and prognostics, biotechnology, gene therapy, research, pharmaceuticals);

(e) minerals such as for benfication of ores, environmental samples, diagnostic and prognostic samples (such as deposits, bone, etc.);

(f) for space medicine (gravity-, centrifuge-, large magnet-free separations);

(g) cellular organelles and other biological structures including, nuclei, chromosomes, ribosomes mitochondria endosomes, blebs, peroxisomes, and other liposomal entities membranes associations including endoplasmic reticulum, plasma membrane, nuclear membrane, viral capsules, bacterial complexes, spore assemblies, etc.; and (h) cells, organelles or other particles with respect to the extent of binding to labels. (For example, different cell subpopulations characterized by different numbers of EGF receptors may be discriminated by labels modified with monoclonal antibodies for EGF).

TABLE 1

(1) $F_{DEP} = 2\pi\varepsilon_s R^3 f_{cm}(\varepsilon_s^*, \varepsilon_p^*, \omega_E)\nabla E(x, y, z)^2$ (2) $F_{MAP} = 2\pi\mu_s R^3 k_{cm}(\mu_s^*, \mu_p^*, \omega_H)\nabla H(x, y, z)^2$ (3) $F_{MAP} = \mu_s R^3 \overline{m}\nabla \cdot H(x, y, z)$ (4) $F_{DEP} = F_{DEPo} e^{-h/h_{DLP}}$ (5) $F_{MAP} = F_{MAPo} e^{-h/h_{MAP}}$ (6) $F_{DEP} + F_{MAP} = 2\pi\varepsilon_s R^3 f_{cm}(\varepsilon_s^*, \varepsilon_p^*, \omega) G_{DEP} V_o^2 e^{-h/h_{DEP}} +$
$2\pi\mu_s R^3 k_{cm}(\mu_s^*, \mu_p^*, \omega) G_{MAP} B_o^2 e^{-h/h_{MAP}}$
$= 0$ (7) $\dfrac{\varepsilon_s f_{cm}(\varepsilon_s^*, \varepsilon_p^*, \omega_E) G_{DEP} V_o^2}{\mu_s k_{cm}(\mu_s^*, \mu_p^*, \omega_H) G_{MAP} B_o^2} = e^{h\left(\frac{h_{DEP} - h_{MAP}}{h_{DEP} h_{MAP}}\right)}$ (8) giving $h = \left(\dfrac{h_{DEP} h_{MAP}}{h_{DEP} - h_{MAP}}\right)\ln\left\{\dfrac{\varepsilon_s f_{cm}(\varepsilon_s^*, \varepsilon_p^*, \omega_E) G_{DEP} V_o^2}{\mu_s k_{cm}(\mu_s^*, \mu_p^*, \omega_H) G_{MAP} B_o^2}\right\}$ (8a) $F_{DEP} + F_{MAP} = 2\pi\varepsilon_s R^3 f_{cm}(\varepsilon_s^*, \varepsilon_p^*, \omega) G_{DEP} V_o^2 e^{-h/h_{DEP}} +$
$\mu_s R^3 \overline{m}(\mu_s^*, \mu_p^*, \omega) G_{MAP} B_o^2 e^{-h/h_{MAP}}$
$= 0$ (9) $\dfrac{2\pi\varepsilon_s f_{cm}(\varepsilon_s^*, \varepsilon_p^*, \omega_E) G_{DEP} V_o^2}{\overline{m} G_{MAP} B_o} = h\left(\dfrac{h_{DEP} - h_{MAP}}{h_{DEP} h_{MAP}}\right)$

(10) giving $h = \left(\dfrac{h_{DEP} h_{MAP}}{h_{DEP} - h_{MAP}}\right)\ln\left\{\dfrac{2\pi\varepsilon_s f_{cm}(\varepsilon_s^*, \varepsilon_p^*, \omega_E) G_{DEP} V_o^2}{\overline{m} G_{MAP} B_o^2}\right\}$

(11) $v(h) = \dfrac{1}{6}\langle v\rangle\dfrac{h}{D}\left(1 - \dfrac{h}{D}\right)$ All of the compositions and/or methods disclosed and claimed herein can be made and executed without undue experimentation in light of the present disclosure. While the compositions and methods of this invention have been described in terms of specific embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of discriminating matter utilizing dielectrophoresis combined with magnetophoresis, comprising:
   injecting a sample having one or more constituents into an inlet port of a chamber;
   initiating a carrier medium flow at the inlet port to establish a flow within the chamber;
   generating a dielectrophoretic force on the constituents;
   generating a magnetic force on the constituents;
   balancing the dielectrophoretic force and magnetic force to position the constituents at characteristic equilibrium positions within the chamber; and
   collecting the constituents at one or more outlet ports of the chamber according to the dielectric and magnetic characteristics of the constituents.

2. The method of claim 1, wherein the sample comprises one or more analytes mixed with one or more labels having distinguishable magnetic and dielectric properties.

3. The method of claim 2, wherein a first label has first dielectric and magnetic properties and has a binding affinity for a first analyte and a second label has second dielectric and magnetic properties and has a binding affinity for a second analyte.

4. The method of claim 1, wherein the carrier medium flow causes the constituents to travel at velocities dependent upon their positions within the chamber.

5. The method of claim 4, wherein collecting comprises collecting different constituents emerging at different times from the one or more outlet ports according to their dielectric and magnetic characteristics.

6. The method of claim 1, wherein collecting comprises collecting different constituents emerging at different positions from the one or more outlet ports according to their dielectric and magnetic characteristics.

7. A method for batch-mode discrimination of matter utilizing dielectrophoresis combined with magnetophoresis, comprising:
   injecting an aliquot of a sample having one or more constituents into an inlet port of a chamber;
   initiating a carrier medium flow at the inlet port to establish a flow within the chamber, wherein the carrier medium flow causes the constituents to travel at velocities dependent upon their positions within the chamber;
   generating a dielectrophoretic force on the constituents;
   generating a magnetic force on the constituents;
   balancing the dielectrophoretic force and magnetic force to position the constituents at characteristic equilibrium positions within the chamber; and
   collecting the constituents according to time-of-exit from an outlet port of the chamber.

8. The method of claim 7, wherein the sample comprises one or more analytes mixed with one or more labels having distinguishable magnetic and dielectric properties.

9. The method of claim 8, wherein a first label has first dielectric and magnetic properties and has a binding affinity for a first analyte, and a second label has second dielectric and magnetic properties and has a binding affinity for a second analyte.

10. A method for continuous-mode discrimination of matter utilizing dielectrophoresis combined with magnetophoresis, comprising:
   continuously injecting a sample having one or more constituents into an inlet port of a chamber;
   initiating a carrier medium flow at the inlet port to establish a flow within the chamber;
   generating a dielectrophoretic force on the constituents;
   generating a magnetic force on the constituents;
   balancing the dielectrophoretic force and magnetic force to position the constituents at characteristic equilibrium positions within the chamber; and
   collecting the constituents from a plurality of outlet ports of the chamber according to the positions of the constituents.

11. The method of claim 10, wherein the sample comprises one or more analytes mixed with one or more labels having distinguishable magnetic and dielectric properties.

12. The method of claim 11, wherein a first label has first dielectric and magnetic properties and has a binding affinity for a first analyte, and a second label has second dielectric and magnetic properties and has a binding affinity for a second analyte.

13. A method of discriminating matter utilizing dielectrophoresis combined with magnetophoresis, comprising:
   providing a chamber comprising at least one inlet and one outlet port, an array of electrodes in operative relation with to the chamber and configured to generate a dielectrophoretic force, and one or more permanent magnets in operative relation with the chamber and configured to generate a magnetic force;
   injecting matter into an inlet port of a chamber;
   generating a magnetic force on the matter using the one or more permanent magnets to discriminate and collect matter upon the magnets;
   generating a dielectrophoretic force using the electrodes to repel the collected matter from the magnets; and
   collecting the matter at one or more outlet ports of the chamber.

14. A method of discriminating matter utilizing dielectrophoresis and magnetophoresis, comprising:
   preparing a sample containing at least one analyte and a plurality of labels, the plurality of labels having preselected dielectrophoretic and magnetic properties, at least some of the plurality of labels combining with the at least one analyte to create analyte-label complexes;
   injecting the sample into an inlet port of a chamber, the chamber comprising a separation channel;
   providing an electrical signal to at least one electrode element adapted to the chamber at different phases to create an electric field in the chamber to cause a dielectrophoretic force on the sample;
   providing a magnetic signal to at least one magnetic element adapted to the chamber to create a magnetic field in the camber to cause a magnetophoretic force on the sample;
   balancing the dielectrophoretic force and magnetophoretic force to position constituents of the sample at characteristic equilibrium positions within the chamber;
   initiating a carrier medium flow at the inlet port to establish a hydrodynamic flow profile within the separation channel, the carrier medium causing the at least one analyte and the analyte-label complexes to travel at velocities dependent upon their positions within the separation channel;
   collecting the analyte-label complexes at an outlet port of the chamber, wherein the analyte-label complexes having similar magnetic and dielectric properties arrive at the outlet port in a single elution peak.

15. A method of discriminating target analytes utilizing dielectrophoresis and magnetophoresis, comprising:
   preparing a sample containing at least one analyte and a plurality of labels, the plurality of labels having preselected dielectrophoretic and magnetic properties, at least some of the plurality of labels combining with the at least one analyte to create analyte-label complexes;
   providing an electrical signal to at least one electrode element adapted to a chamber comprising a separation channel at different phases to create an electric field in the chamber to cause a dielectrophoretic force on the sample;
   providing a magnetic signal to at least one magnetic element adapted to the chamber to create a magnetic field in the chamber to cause a magnetophoretic force on the sample;
   balancing the dielectrophoretic force and magnetophoretic force to position constituents of the sample at characteristic equilibrium positions within the chamber;
   continuously injecting the sample into an inlet port of the chamber;
   collecting the analyte-label complexes at a plurality of outlet ports of the chamber, wherein the analyte-label complexes having similar magnetic and dielectric properties arrive at the same one of the plurality of outlet ports.

16. An apparatus for discrimination of a sample utilizing dielectrophoresis, magnetophoresis, and field flow fractionation, comprising:
   a chamber having at least one inlet and one outlet port;
   an array of electrodes in operative relation with the chamber and configured to generate a dielectrophoretic force upon constituents of sample within the chamber;
   an array of magnetrodes in operative relation with the chamber and configured to generate a magnetic force upon constituents of the sample within the chamber; and
   wherein the electrodes and magnetrodes are configured to generate forces that balance one another to displace constituents within the sample to equilibrium positions within the chamber characteristic of their magnetic and dielectric properties.

17. The apparatus of claim 16, wherein the array of magnetrodes comprises one or more permanent magnets.

18. The apparatus of claim 16, wherein the outlet port comprises multiple ports configured to collect bands of fluid that travel through the chamber at defined positions.

* * * * *